United States Patent [19]

Sepetka et al.

[11] Patent Number: 5,356,388
[45] Date of Patent: Oct. 18, 1994

[54] PERFUSION CATHETER SYSTEM

[75] Inventors: Ivan Sepetka, Redwood City; Phong Pham, San Jose, both of Calif.

[73] Assignee: Target Therapeutics, Inc., Fremont, Calif.

[21] Appl. No.: 948,720

[22] Filed: Sep. 22, 1992

[51] Int. Cl.5 .................... A61M 5/178; A61M 5/00
[52] U.S. Cl. .................... 604/164; 604/280; 604/282; 604/256; 604/264
[58] Field of Search ............... 604/164, 166, 170, 264, 604/256, 270, 280, 281, 282

[56] References Cited

U.S. PATENT DOCUMENTS

| | | | |
|---|---|---|---|
| 3,841,308 | 10/1974 | Tate | 604/282 |
| 4,655,771 | 5/1987 | Wallsten | 604/281 |
| 4,863,442 | 9/1989 | DeMello et al. | 604/282 |
| 5,069,217 | 12/1991 | Fleischhacker | 604/282 |
| 5,174,302 | 12/1992 | Palmer | 604/164 |

*Primary Examiner*—John G. Weiss
*Attorney, Agent, or Firm*—Morrison & Foerster

[57] ABSTRACT

A catheter for use in combination with a guide wire for placement within a tortuous, small vessel and delivery of fluid at a target site is disclosed. The catheter comprises an elongate tubular body with a perforated flexible tip located at the distal end of the elongate tubular body.

10 Claims, 3 Drawing Sheets

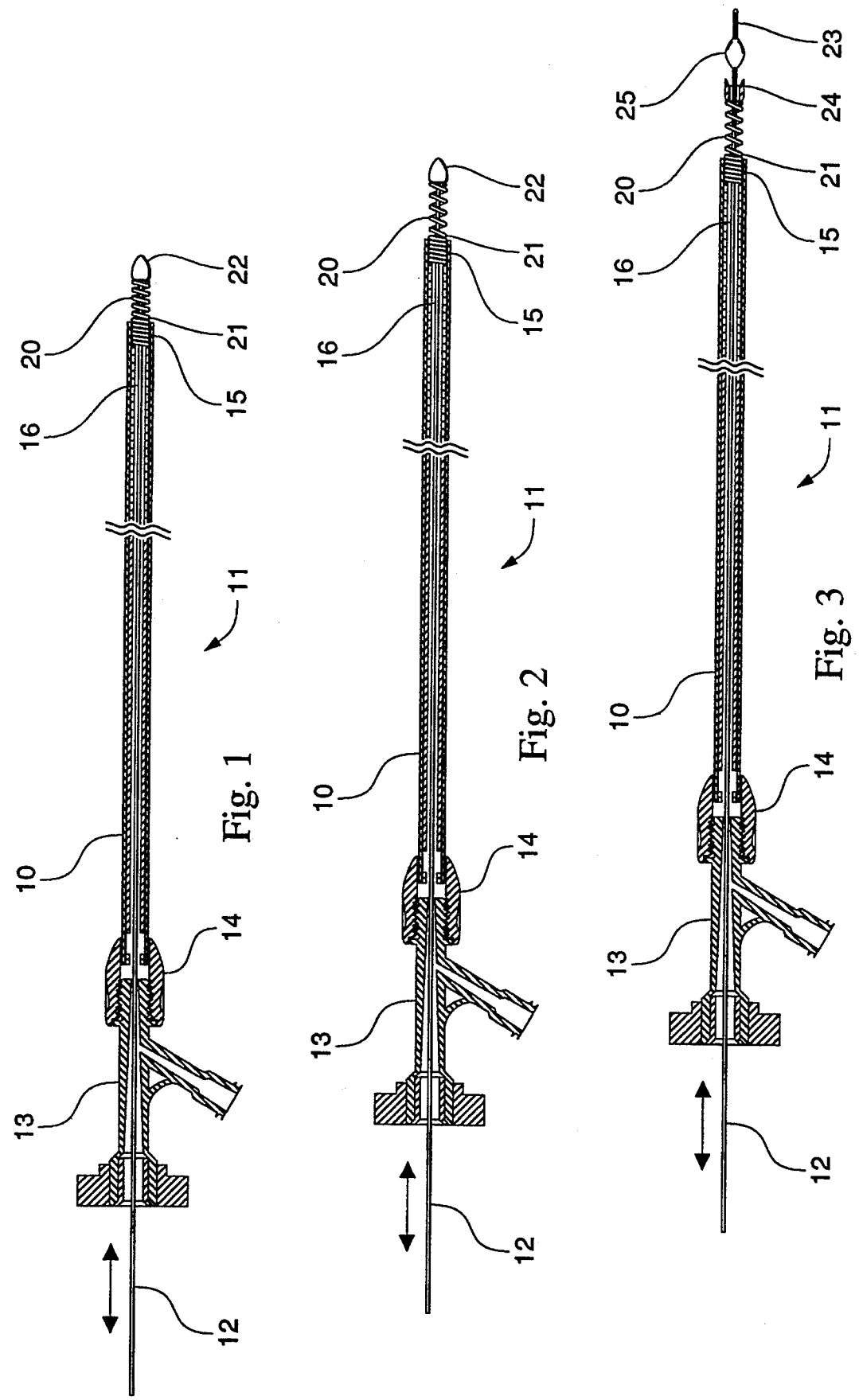

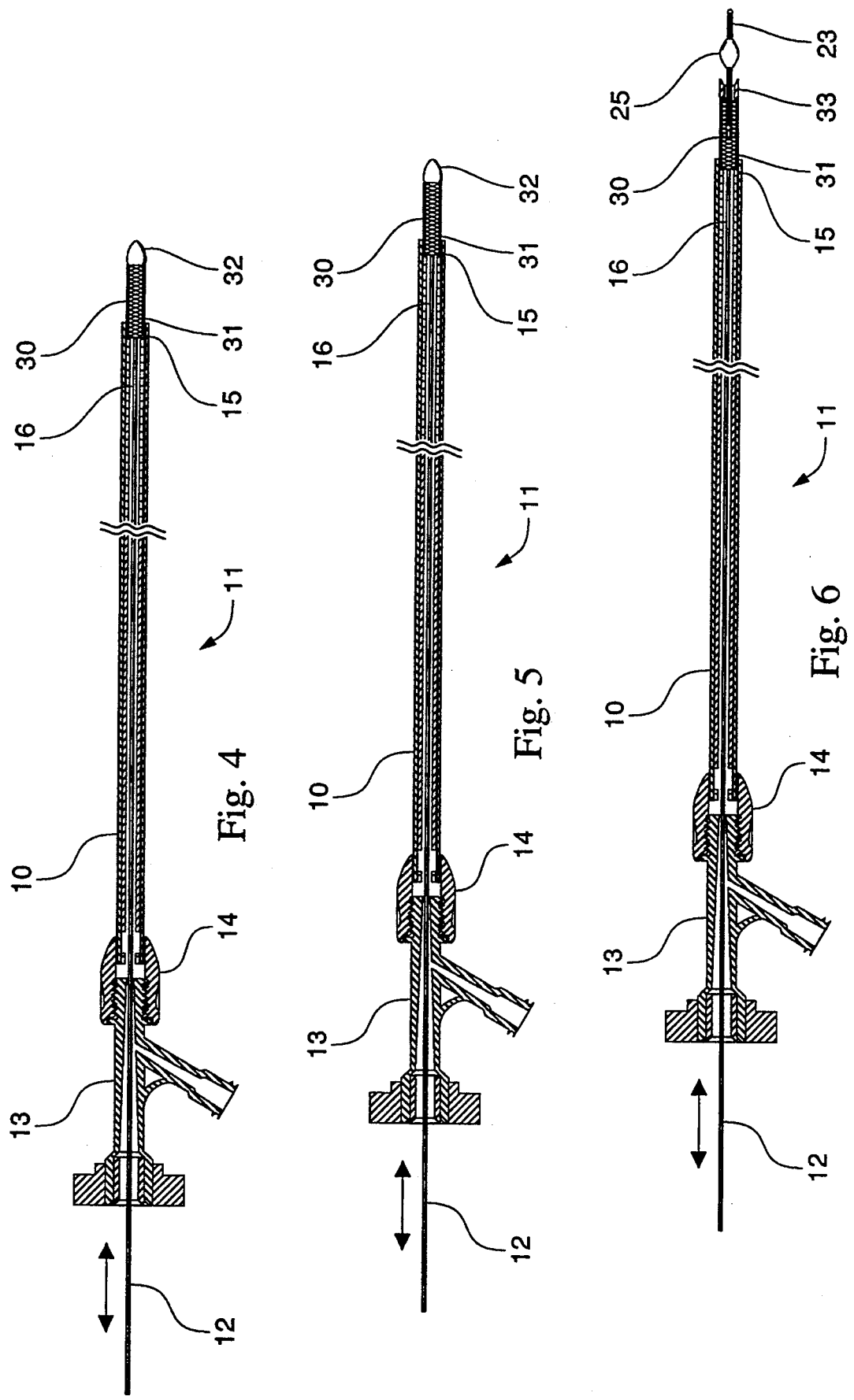

PERFUSION CATHETER SYSTEM

FIELD OF THE INVENTION

This invention is a surgical instrument and specifically is both a catheter for treating a target site by delivering a controlled amount of a therapeutic or diagnostic agent (the target site being accessible by a tortuous path through the vasculature) and a process of using that catheter.

BACKGROUND OF THE INVENTION

Catheters are being used increasingly as a means for delivering diagnostic or therapeutic agents to internal target sites that can be accessed through the circulatory system. For example, in angiography, catheters are designed to deliver a radio-opaque agent to a target site within a blood vessel, to allow radiographic viewing of the vessel and of the blood flow characteristics near the release site. For the treatment of localized disease, such as solid tumors, catheters allow a therapeutic agent to be delivered to the target site at a relatively high concentration with minimum overall side effects. Methods for producing localized vaso-occlusion in target tissue regions, by catheter injection of a vaso-occlusive agent have also been described (U.S. Pat. No. 4,708,718 for "Hyperthermic Treatment of Tumors").

U.S. Pat. No. 4,739,768 describes a catheter having a guide wire. The catheter may be guided from an external body access site such as through the femoral artery, to an internal tissue site. The catheter progresses through a tortuous path of at least about 5 cm through vessels of less than about 3 mm inner diameter. The catheter has a relatively stiff segment dimensioned to track the wire from the access site to a region adjacent the internal tissue, and a relatively flexible remote segment dimensioned to track the wire along the tortuous path within the soft tissue. In a method for injecting a fluid into a tortuous path site, the guide wire and catheter are moved as a unit to a position adjacent the target tissue. The wire is then advanced ahead of the catheter along the tortuous path within the tissue. The catheter then tracks the wire to move along the wire's path. Once the tip of the catheter reaches the chosen site, the guide wire is removed and the selected treatment or diagnostic fluid is delivered to the target site.

The present invention is a catheter assembly useful for the delivery of diagnostic or therapeutic agents to remote portions of the vascular system, particularly to diagnose or to treat intravascular occlusions that result from embolus or thrombus formation. The invention also includes a process for delivering fluids to those vascular regions by controlling the exit rate at the remote tip.

SUMMARY OF THE INVENTION

This invention is a catheter for use in combination with a guide or core wire for placement within a tortuous, small vessel and for delivery of fluid at a target site. The catheter has an elongate tubular body having proximal and distal ends and a lumen extending between the ends containing the guide wire. The tubular body also has a flexible tip located at the remote or distal end for tracking the wire along the tortuous path, through small vessels to a target site and for delivery of fluid at the target site.

A further aspect of the invention is a method for delivering a controlled amount of a therapeutic or diagnostic agent. The method involves the placement of a catheter at a remote site in the vasculature and the delivery of the agent through the flexible tip of the catheter which is positioned at the target site.

BRIEF DESCRIPTION OF THE DRAWINGS

FIG. 1 shows a catheter with a coil tip constructed according to one embodiment of the present invention, and a guide wire used in guiding the catheter to a tortuous-path target site.

FIG. 2 shows a catheter with a coil tip constructed according to a second embodiment of the present invention, and a guide wire used in guiding the catheter to a tortuous-path target site.

FIG. 3 shows a catheter with a coil tip constructed according to a third embodiment of the present invention, and a guide wire used in guiding the catheter to a tortuous-path target site.

FIG. 4 shows a catheter with a braided tip constructed according to a fourth embodiment of the present invention, and a guide wire used in guiding the catheter to a tortuous-path target site.

FIG. 5 shows a catheter with a braided tip constructed according to a fifth embodiment of the present invention, and a guide wire used in guiding the catheter to a tortuous-path target site.

FIG. 6 shows a catheter with a braided tip constructed according to a sixth embodiment of the present invention, and a guide wire used in guiding the catheter to a tortuous-path target site.

FIG. 7 is a closeup of the coil tip.

DESCRIPTION OF THE INVENTION

Figure 7A:
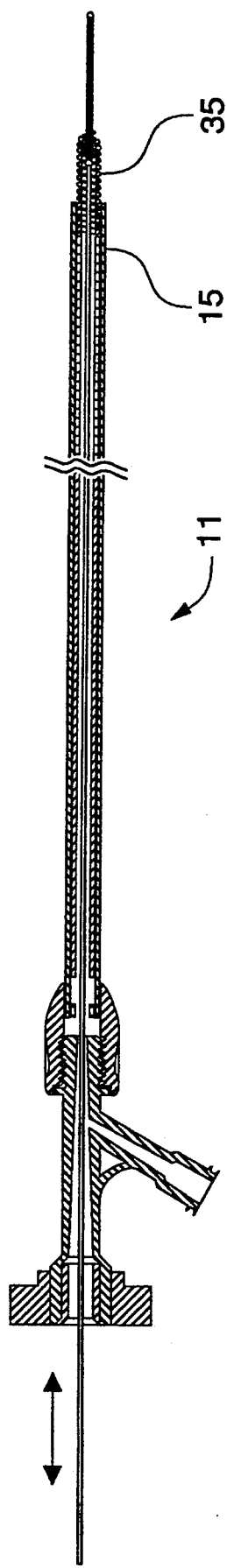
FIG. 7A and 7B show an embodiment of the invention in which the catheter has a coiled tip suitable for remote delivery of a fluid through that tip. The core wire in the portrayed variation extends through the coiled tip and is removable through the center of the tubular body.

The catheter assembly of the present invention has a core or guide wire and an elongate tubular body. The elongate tubular body has a relatively stiff proximal segment such that the catheter can more easily track the wire along the tortuous vessel pathway. The flexible segment has a flexible perfusion tip which allows a controllable desired flow of fluid to a selected target site within the vasculatureo The perfusion tip is made of a material that is springy, biologically compatible, and (desirably) is visible when exposed to x-ray. Examples of suitable materials are polymers, metals, and alloys; particularly appropriate are materials such as various stainless steels, platinum, platinum alloys, plated metals, plastics, Inconel, and Nitenol. The perfusion tip is constructed in such a way that fluids introduced into the catheter at the proximal end perfuse out of openings in the tip. The tip may be in the form of a coil wound from wire or ribbon, a braid or other appropriate configurations in which the size of the openings in the perfusion tip are remotely controllable from the proximal end of the catheter. If the perfusion tip is in the form of a coil, the coil windings may be regular or variable depending upon the desired fluid delivery characteristics. The flow of fluid may be held constant or may be remotely controlled as will be described below.

The following representative embodiments are illustrative only and in no way limit the invention.

FIG. 1 shows one embodiment of a catheter assembly of the invention. The assembly is generally designated 10, and includes a catheter 11 in combination with a guide wire 12. The assembly includes a standard proximal end fitting 13 through which the guide wire is received and to which the proximal end 14 of the catheter is removable attached. As depicted, the catheter is a continuous tubular body that extends from proximal end 14 to distal end 15 and through which the guide wire extends.

The catheter may be constructed of any suitable materials which allow for sufficient flexibility to navigate the tortuous path through small vessels. A variable stiffness catheter is described in U.S. patent application Ser. No. 07/741,775, filed Aug. 7, 1991. The catheter has proximal and distal ends and a lumen extending therebetween for receiving the guide wire. The body comprises an outer coaxial tube extending continuously between the ends having a wall thickness of 0.002 to 0.020 inches and being made of a polymer having a flexural modulus of about 2000 to 5000 kpa, and proximal, intermediate, and distal inner coaxial polymeric tube segments positioned contiguously in tandem within the outer tube from the proximal end to a site proximal the distal end. The proximal segment has a wall thickness of 0.002 to 0.020 inches and is made of a polymer having a flexural modulus of about 32,000 to 38,000 kpa. The intermediate segment desirably is less stiff than the proximal segment and the distal segment is desirably less stiff than the intermediate segment but stiffer than the portion of the outer tube extending from the site to the distal end.

At the distal end of the catheter is found a perfusion tip, a coil 20. The proximal end 21 of the coil is fused onto the distal end 15 of the catheter. The distal end 22 of the coil is formed, such as by soldering or melding or welding or other forming process, to create a smooth, rounded tip. The outer diameter of the coil will normally be 0.002 to 0.020 inches and the overall length of the tightly wound coil will normally be between two and 100 mm. The coil is formed from materials that are springy, biologically compatible, and preferably visible when exposed to x-ray, and may be selected from an appropriate metal or alloy such as stainless steel, platinum, platinum alloys (particularly platinum-tungsten), Inconel, or Nitinol, but is preferably a platinum-tungsten wire with an outer diameter between 0.001 and 0.010 inches. The coil may be wound such that the pitch is constant or variable, as the particular application requires, but is preferably wound in a variable pitch as depicted in FIG. 1 to allow for better fluid control.

In operation, the core wire 12 is inserted into the lumen of the catheter 11 such that the distal end 16 of the guide wire abuts the rounded tip 22 of the perfusion coil 20. The assembly is guided through the vasculature to the target site and the guide wire is removed. Fluid is then injected through the proximal end fitting 13 and into the catheter lumen. The fluid perfuses out through the perfusion coil 20 and into the target site at the desired rate. The fluid may be a radiopaque agent, a chemotherapeutic agent, a clot dissolving agent, a vasoocclusive agent, or any similar fluid which must be delivered to the target site.

FIG. 2 shows a second embodiment of a catheter assembly of the invention. The catheter 11, core wire 12, proximal end fitting 13 and coil 20 are as described in connection with FIG. 1. Again, the proximal end 21 of the perfusion coil is fused into the distal end 15 of the catheter. The distal end 22 of the perfusion coil is formed to create a smooth, rounded tip. The distal end of core wire 12 is soldered to the rounded tip at the distal end 22 of the perfusion coil. In this way, the coil tip/guide wire portion of the assembly provides support for the advancement of the system through the vasculature. In addition, when fluid is injected through the proximal end fitting 13 and into the catheter, the perfusion coil tip 20 may be compressed or stretched by pulling or pushing on the proximal end of the guide wire. When the guide wire 12 is pulled and the coil thereby compressed, the flow rate of liquid through the coil is decreased but will create jet of liquid against the target. When the guide wire 12 is pushed and the coil 20 thereby stretched, the flowrate of liquid through the coil is increased and causes slow dripping of the delivered liquid.

FIG. 3 shows a third embodiment of a catheter assembly of the invention. The catheter 11, proximal end fitting 13 and guide wire 12 are as described in connection with FIG. 1. In this embodiment, however, the guide wire 12 extends through the proximal end fitting 13, through the catheter lumen and beyond the distal end 15 of the catheter lumen. The distal end 23 of the guide wire functions as a valve. It has a plug or bead 25 which acts to at least partially seal the distal end 24 of the perfusion coil 20. The proximal end 21 of the coil is fused into the tip of the catheter. The distal end 24 of the perfusion coil 20 is open and dimensioned so that when the plug 25 on the distal end 23 of the guide wire is seated against the perfusion coil, the end of the coil may be sealed and liquid will not perfuse out the distal end of the coil.

The physical configuration of the perfusion coil 20, i.e., outer diameter, overall length, materials of construction, are as described above. The coil may be wound such that the pitch is constant or variable, as the particular application requires, but is preferably wound in a variable pitch as depicted in FIG. 3. In this embodiment, the distal portion of the guide wire provides support for the advancement of the system through the vasculature. In addition, when fluid is injected through the proximal end fitting and into the catheter, the perfusion coil tip may be compressed by pulling on the proximal end of the guide wire. In this way, the flow rate of liquid through the perfusion coil will be decreased and create the required jet control of drug delivery.

FIG. 4 shows a fourth embodiment of a catheter assembly of the invention. The catheter 11, guide wire 12, and proximal end fitting 13 are as described in connection with FIG. 1. Rather than a coil, the distal end 15 of the catheter comprises a braided perfusion tube 30. The proximal end 31 of the braided perfusion tube 30 is fused into the tip of the catheter. The distal end 32 of the braided perfusion tube 30 is formed, as by soldering, to create a smooth, rounded tip. The outer diameter of the braided perfusion tube will normally be 0.010 to 0.015 inches and the overall length will normally be between 2 and 100 mm. The braided tube is formed from materials that are springy, biologically compatible, and desirably visible when exposed to x-rays, and may be selected from any appropriate metal alloy such as stainless steel, platinum, platinum alloys (such as platinum-tungsten), Inconel, or Nitinol, but is preferably platinum-tungsten wire with an outer diameter between 0.0005 and 0.005 inches. The wire may be braided in such as way as to provide constant or variable pitch. In this variation, as with all of the others, the coil or braid may be a polymer which is woven or braided into an appropriate form.

The operation of this embodiment is analogous to that of shown in connection with FIG. 1. The core wire 12 is inserted into the lumen of the catheter such that the distal end 16 of the guide wire abuts the rounded tip 32 of the braided perfusion tube. The assembly is guided through the vasculature to the target site and the guide wire is removed. Fluid is then injected through the proximal end fitting 13 and into the catheter lumen. The fluid perfuses out through the braided perfusion tube 30 and into the target site at the desired rate.

FIG. 5 shows a fifth embodiment of a catheter assembly of the invention. The catheter 11, core wire 12, and proximal end fitting 13 are as described in connection with FIG. 2. Rather than a coil, the distal end of the catheter comprises a braided perfusion tube 30. The proximal end 31 of the braided tube is fused into the tip 15 of the catheter. The distal end 32 of the braided tube is formed to create a smooth, rounded tip. The outer diameter of the braided perfusion tube 30 will normally be 0.010 to 0.015 inches and the overall length will normally be between 2 and 100 mm. The braided tube may be formed from materials such as those described above.

The distal end 16 of the core wire is connected to the rounded tip 32 of the braided perfusion tube 30. In this way, the braided tube/guide wire portion of the assembly provides support for the advancement of the system through the vasculature. In addition, when fluid is injected through the proximal end fitting 13 and into the catheter 11, the braided tube may either be compressed or stretched by pulling or pushing on the proximal end of the guide wire.

Depending upon the weave chosen for the braid of the braided perfusion tube 30, movement of the core wire may have a variety of results upon the flow rate through the braid wall. For instance, if the braid configuration is normally loose—that is, the braid allows flow through the wall when no tension is placed on the axis of the tube by the core wire—pulling on the core wire a short distance will increase the perfusion flow though the braid wall. Pulling farther on the core wire will increase the diameter of the braid and the openings will begin to close. Similarly, pushing on the core wire from the initial or rest position will close the openings in the braid wall.

If the braid is woven in such a way that the braid (at the "rest" position) does not allow perfusion flow, movement of the core wire by pulling will open the gaps between the various braid wires allowing increased flow. Pushing the core wire would have little effect.

FIG. 6 shows a sixth embodiment of a catheter assembly of the invention. The catheter 11, guide wire 12, and proximal end fitting 13 are as described in connection with FIG. 1. Rather than a coil, the distal end 15 of the catheter comprises a braided perfusion tube 30. The proximal end 31 of the braided perfusion tube 30 is fused into the tip 15 of the catheter. The distal end 33 of the braided tube is open and dimensioned so that when the plug situated on the distal end 23 of the guide wire is seated against the braided tube, the tube is sealed and liquid will not perfuse out the distal end 33 of the tube. The braided tube 30 is formed from materials that are springy, biologically compatible, and visible when exposed to x-ray, and may be selected from any appropriate metal alloy such as stainless steel, platinum, Inconel, or Nitenol, but is preferably a platinum-tungsten alloy wire with an outer diameter between 0.001 and 0.010 inches. The wire may be braided in such as way as to provide constant or variable pitch.

In this embodiment, the distal portion 23 of the guide wire provides support for the advancement of the system through the vasculature. In addition, when fluid is injected through the proximal end fitting 13 and into the catheter 11, the braided tube 30 may be compressed by pulling on the proximal end of the guide wire. In this way, the flow rate of liquid through the tube will be increased.

Figure 7B:
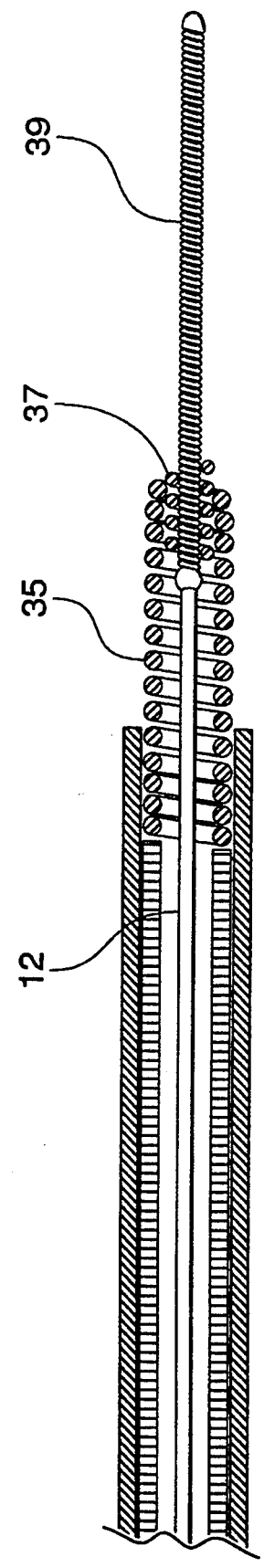

FIGS. 7A and 7B show another embodiment of the invention in which the core wire extends through the end of the perfusion tip in a guide tip and that core wire is removable, may be disconnected from the perfusion tip to facilitate introduction of the catheter into the vascular system, or may be fixedly attached to the distal end of the perfusion tip.

Specifically, FIG. 7A includes a catheter assembly as has been shown above. The catheter 11, core wire 12, and proximal end fitting 13 are all as shown in FIG. 1. As is shown in FIG. 7B, the perfusion tip is a coil 35, which is fixedly joined to the distal tip 15 of the catheter. The distal end of the perfusion coil 35 is adapted to accept a smaller threaded interlock 37. The distal and of the perfusion coil depicted in FIG. 7B is crimped so that it connects with the interlock only for a couple of turns. The interlock 37 forms an interface between the perfusion coil 35 and the guide wire tip 39. The interlock 37 is threaded on its outer surface to engage the inner surface of the perfusion tip 35. The interlock 37 may be threaded on its inner surface to engage the outer surface of the guide tip 39 but typically is fixed to the guide tip 39 for ease of operation. The perfusion coil 35 is of the mechanical design and materials specified above. In operation, the guide wire 12 is pulled or pushed to open or close the openings in the perfusion coil as has been discussed at length above. However, by turning the guide wire, the interlock 37 moves one way or the other through the perfusion coil 35. Twisting one way will move the interlock 37 and the guide tip 39 into the perfusion coil 35 and, upon further twisting, will move through out the perfusion coil 35 into the lumen of the catheter. During the traverse through the perfusion coil 35, the interlock 37 effectively lowers the area through which the perfusive fluid will flow. So, in addition to the effective control of flow rate from the perfusion coil 35 provided by the movement of the guide wire axially through the perfusion coil, this variation of the invention provides additional control upon that flow by blocking portions of the perfusion coil.

Additionally, when the guide wire 12 is twisted in the opposite direction, the interlock 37 is twisted out the distal end of the perfusion coil 35.

Modifications of the above described modes for carrying out the invention that are obvious to those of skill in the mechanical and guide wire/catheter arts are intended to be within the scope of the following claims.

We claim:

1. A catheter for placement within a tortuous, small vessel and for delivery of fluid at a target site, said catheter comprising an elongate tubular body having proximal and distal ends and a lumen extending between said ends, said catheter comprising:
   (a) a polymeric tube extending continuously from said elongate tubular body proximal end to a perfusion tip attached distally of said polymeric tube, said tube being small enough and stiff enough to be guided through the tortuous small vessel; and (b) a perfusion tip attached distally of the polymeric tube and having adjustable perfusion openings which are remotely adjustable so to allow a remotely controllable delivery rate of fluid at the target site.

2. The catheter of claim 1 wherein the perfusion tip comprises a member selected from, platinum, Inconel, and Nitinol or plastics.

3. The catheter of claim 1 wherein the perfusion tip is a coil.

4. The catheter of claim 3 additionally comprising a core wire which may be removed to allow for injection of fluid into the catheter lumen and through the perfusion tip to the target site.

5. The catheter of claim 3 additionally comprising a core wire is affixed to the tip of the coil such that when the core wire is pushed or pulled, the coil will be compressed or stretched for controlling flow rate of fluid to the target site.

6. The catheter of claim 3 additionally comprising a core wire which extends through the tip of the coil and a plug is affixed to the distal end of the core wire such that when the plug is seated at the distal end of the coil, fluid injected into the catheter lumen will flow through the coil for controlled delivery to the target site.

7. The catheter of claim 1 wherein the perfusion tip is braided tube.

8. The catheter of claim 7 additionally comprising a core wire which is removable in order to allow for injection of fluid into the catheter lumen and through the braided tube to the target site.

9. The catheter of claim 7 additionally comprising a core wire which is affixed to the tip of the braided tube such that when the guide wire is pushed or pulled, the braided tubing will be compressed or stretched for controlling the flow rate of fluid to the target site.

10. The catheter of claim 7 additionally comprising a core wire which extends through the tip of the braided tubing and a plug is affixed to the distal end of the core wire such that when the plug is seated at the distal end of the braided tubing, fluid that is injected into the catheter lumen will flow through the braided tube for controlled delivery to the target site.

* * * * *

UNITED STATES PATENT AND TRADEMARK OFFICE
CERTIFICATE OF CORRECTION

PATENT NO. : 5,356,388
DATED : October 18, 1994
INVENTOR(S) : SEPETKA et al.

It is certified that error appears in the above-indentified patent and that said Letters Patent is hereby corrected as shown below:

In claim 2, column 7, line 7 of the Patent, insert --stainless steel-- after the word "from".

Signed and Sealed this

Sixteenth Day of April, 1996

Attest:

BRUCE LEHMAN

*Attesting Officer*     *Commissioner of Patents and Trademarks*